US005763650A

United States Patent [19]
Mauro et al.

[11] Patent Number: 5,763,650
[45] Date of Patent: Jun. 9, 1998

[54] PROCESS FOR THE PREPARATION OF A HALOSUBSTITUTED AROMATIC ACID

[75] Inventors: Marina Mauro; Carlo Felice Viscardi; Massimo Gagna, all of Mozzo, Italy

[73] Assignee: Fructamine S.p.A., Mozzo, Italy

[21] Appl. No.: 645,448

[22] Filed: May 13, 1996

[30] Foreign Application Priority Data

May 23, 1995 [IT] Italy .................................. MI95A1045
Aug. 4, 1995 [IT] Italy .................................. RM95A0549

[51] Int. Cl.$^6$ .................................................. C07C 229/00
[52] U.S. Cl. ................................................ 562/456
[58] Field of Search .................................... 562/456

[56] References Cited

U.S. PATENT DOCUMENTS 4,102,917  7/1978  Conrow .............................. 260/506

OTHER PUBLICATIONS

Derwent abstract 91-298751—"JP 03197451".
Derwent abstract 89-102353—"JP 01047746".

*Primary Examiner*—Samuel Barts
*Attorney, Agent, or Firm*—Nixon & Vanderhye P. C.

[57] ABSTRACT

The present invention refers to a process for the preparation of 5-amino-2,4,6-triiodo-1,3-benzenedicarboxylic acid, comprising the following steps:

a) catalytic hydrogenation of 5-nitro-1,3-benzenedicarboxylic acid in neutral or basic environment, which gives an aqueous solution of 5-amino-1,3-benzenedicarboxylic acid sodium salt;

b) direct iodination of the 5-amino-1,3-benzenedicarboxylic acid sodium salt solution deriving from step a), without further purification, with a solution of ICl in HCl, being the 5-amino-1,3-benzenedicarboxylic acid sodium salt solution previously added with HCl and $H_2SO_4$.

8 Claims, No Drawings

PROCESS FOR THE PREPARATION OF A HALOSUBSTITUTED AROMATIC ACID

This invention refers to a new process for the synthesis of 5-amino-2,4,6-triiodo-1,3-benzenedicarboxylic acid of formula (I)

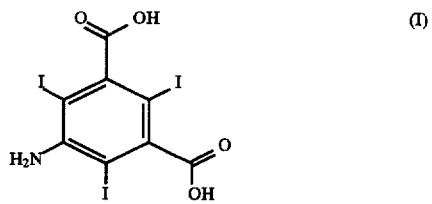

The compound of formula (I) is useful as intermediate for the preparation of iodinated X-ray contrast media, in particular non-ionic ones.

This compound is cited in Beilstein and Chemical Abstracts and its preparation has been described for the first time in patent U.S. Pat. No. 2,820,814 (Schering Corp., 1955; CA 52: 16305; GB-A-785670), by using an excess of iodine monochloride in hydrochloric acid at room temperature. The 5-amino-isophthalic acid (or 5-amino-1,3-benzenedicarboxylic acid) can be directly triiodinated, although one can stepwise iodinate whereby the intermediate mono- or dihalogenated substance is isolated and subjected to further iodination. The resulting reaction yield of 60% is unsatisfactory for the industrial exploitation and, as shown from the example of the above patent, it is necessary to include a purification step, consisting of a treatment with charcoal and further reprecipitation by addition of concentrated hydrochloric acid, thus lowering the final yield.

In a more recent article (J. Org. Chem. 59, 1344, 1994), Ranganathan et al. describe the iodination of the 5-amino-1,3-benzenedicarboxylic acid following a method already known in literature (Larsen et al., J. Am. Chem. Soc., 78, 3210, 1956), using $KICl_2$ generated in situ by reaction between $KIO_3$ and KI in presence of hydrochloric acid. The reaction is carried out at neutral pH and at a temperature of 55°–60° C. with a resulting yield of 74%, always after purification with charcoal and successive reprecipitation by acidification and crystallization by methanol.

In both cited references the purification is necessary since in the final product there are traces of mono- or diiodinated products, as well as the presence of coloured by-products. Both cited processes operate at an extremely low concentration of the starting material.

More recently, some Japanese patent applications have been published (Mitsui Toatsu Chemical Ltd., JP-A-3197451, JP-A-1224203, JP-A-1224202, JP-A-1201002, JP-A-1201003, JP-A-1047746, JP-A-1047745, JP-A-1047744) relative to the preparation and purification of 5-amino-2,4,6-triiodo-1,3-benzenedicarboxylic acid, and the iodine recovery from the mother liquors.

A first patent application JP-A-1047744 describes an improvement of the reaction yield under iodination conditions according to Schering patent, carrying out the reaction at a higher temperature (80°–100° C.), with a resulting declared yield of 97.7%. As deduced from the prior art cited in the successive patent application JP-A-3197451, the resulting product purity is not enough and this application describes the preparation of the above compound by treating 5-aminoisophtalic acid with ICl in presence of $H_2SO_4$ or $H_3PO_4$ as catalyst, to solve this problem.

The acid catalyst is added in amount of 0.1–20 mol %, preferably 1–10% respect to the acid. The concentration of the acid is 1.0–15 wt %, preferably 2.0–10 wt. %. Iodine monochloride is used 3.0–4.5 mol equivalent, preferably 3.0–3.9 mol equivalent to the precursor. The reaction is preferably carried out at 50°–100° C. for 1–5 hours. The final product is obtained with high purity (99.5%) and high yield (98.1%).

The problem which the above application overcomes is the contamination of the product by the intermediates of mono- or di-iodination. The target is achieved by catalysis with sulfuric or phosphoric acid and even without using hydrochloric acid as a solvent for ICl. The patent application does not suggest anything on how to avoid the formation of coloured impurities, which are mentioned in the previous documents and were also present in the product we obtained under the conditions described by the application.

In the experimental section of both applications, the concentration of the substrate has been increased if compared to the previous prior-art references, but is still low if the industrial productivity is taken into account.

In all these references the starting product is isolated 5-amino-1,3-benzenedicarboxylic acid in its indissociate form.

The process of this invention is characterized by the fact that the iodination reaction is carried out directly on 5-amino-1,3-benzenedicarboxylic acid sodium salt, which derives from the catalytic hydrogenation in neutral or basic environment of 5-nitro-1,3-benzenedicarboxylic acid, with a solution of ICl in HCl, which is previously added with HCl and $H_2SO_4$.

Particularly preferred are the following iodination conditions according to which the process of this invention operates:

the ratio of the total acid equivalents coming from HCl and $H_2SO_4$ to the moles of 5-nitro-1,3-benzenedicarboxylic acid ranges from 2.5:1 to 3.5:1;

the ratio of HCl equivalents to 5-nitro-1,3-benzenedicarboxylic acid moles ranges from 0:1 to 2:1, preferably from 0.5:1 to 1.5:1;

the ratio of $H_2SO_4$ equivalents to 5-nitro-1,3-benzenedicarboxylic acid moles ranges from 0.5:1 to 3.5:1, being preferably from 2.0:1;

the molar ratio to ICl and 5-nitro-1,3-benzenedicarboxylic acid ranges from 3.0:1 to 3.5:1;

the molar ratio of HCl to ICl in the ICl solution in HCl ranges from 0.4:1 to 1.2:1;

the temperature of iodination ranges from 75° to 110° C., preferably from 70° to 950° C.

For the first time, due to the presence of the acids in the amounts previously described, it is possible to obtain the desired product as white (hydrate form) or yellow (anhydrous form) crystals with excellent yields and high purity, free from dark coloured compounds, without further purification.

Another remarkable advantage of the presence of sulfuric acid in the amounts previously described, extremely important for the industrial productivity, is the possibility of performing the iodination under conditions of substrate concentration higher than usual standards in the absence of sulfuric acid, with the same yield.

In the experimental section an example is included, in which 3 equivalents of hydrochloric acid without addition of sulfuric acid are added, and an example where only sulfuric acid is added. In the first case a decisively low yield is achieved while in the second case the yield is satisfactory but the final product is dark-brownish, thus requiring a successive purification.

The following examples of the practice of the present invention are meant to be illustrative and are in no way limiting the scope of the invention.

EXAMPLE 1

5-amino-2,4,6-triiodo-1,3-benzenedicarboxylic acid

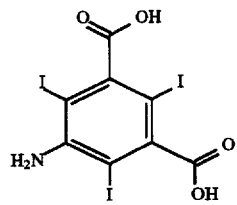

A) 5-amino-1,3-benzenedicarboxylic acid 325 g 5-nitro-1,3-benzenedicarboxylic acid (product available on the market) are loaded into a reactor with 2.8 l of water. It is heated to 60°–700° C. and the starting product dissolved by addition of 410 g of 30% NaOH. Then 10 g of charcoal are added; the slurry is filtered and the filter is washed with 200 ml of water.

8 g of Pd/C 5% (product available on the market) are then loaded and conditioned with approx. 0.01 m³ nitrogen. 0.1 m³ hydrogen are added under a pressure of 30 kPa. The temperature spontaneously reaches 50° C. and is kept by cooling. When the hydrogen consumption stops, the solution is kept under pressure for 1 h and then the residual hydrogen is removed by washing with 0.02 m³ of nitrogen. The suspension is filtered and the filter washed with 100 ml of water giving approx. 3.85 kg of solution containing 5-amino-1,3-benzenedicarboxylic acid sodium salt.

B) 5-amino-2,4,6-triiodo-1,3-benzenedicarboxylic acid

In a reactor loaded with 2.75 l of water, are added in sequence 0.08 kg of HCl (34% w/w), 3.85 kg of solution of 5-amino-1,3-benzenedicarboxylic acid sodium salt coming from the previous reaction and 375 g of $H_2SO_4$ (1:1 aqueous solution). The content is heated to 70° C., and during 3 hours 1.35 kg of a solution of ICl in HCl (44.5% iodine, molar ratio ICl:HCl=1:1) (product available on the market) is added. When the addition is complete the solution is heated to 90° C. and the temperature kept for 6 h. Then the content is cooled to 60° C. and transferred to another reactor, where it is cooled to 30° C. The slurry is decolourised by adding 45 g of sodium bisulfite under stirring, then centrifuged and the product washed with 0.3 kg of water thus giving 935 g of the desired wet product. After drying, 830 g of the desired product are obtained.

Total yield of the two steps (on the anhydrous product): 95.0%
Water content: 2%
Potentiometric assay: 99.3%
¹H-NMR, ¹³C-NMR, IR and MS spectra are consistent with the structure.

EXAMPLE 2

Comparative example of 5-amino-2,4,6-triiodo-1,3-benzenedicarboxylic acid preparation in presence of 3 HCl equivalents.

According to the procedure described in EXAMPLE 1, 3.85 kg of a solution of 5-amino-1,3-benzenedicarboxylic acid sodium salt are reacted with ICl in presence of 0.48 kg of HCl (34% w/w).

Total yield on two steps on anhydrous product: 82.0%

The chemical-physical characteristics are in accordance with those previously described.

EXAMPLE 3

Comparative example of 5-amino-2,4,6-triiodo-1,3-benzenedicarboxylic acid preparation in presence of 3 $H_2SO_4$ equivalents.

According to the procedure described in EXAMPLE 1, 3.85 kg of solution of 5-amino-1,3-benzenedicarboxylic acid sodium salt are reacted with ICl in presence of 450 g of $H_2SO_4$ (1:1 aqueous solution).

Total yield of the two steps on the anhydrous product: 91.0%

The chemical-physical characteristics are in accordance with those previously described, but the product is dark-brownish.

EXAMPLE 4

Comparative example: 5-amino-2,4,6-triiodo-1,3-benzenedicarboxylic acid preparation according to the method described in Example 1 of JP-A-3197451, scale multiplied by 3.

In a jacketed reactor equipped with a stirrer are loaded 57.2 g of 5-amino-1,3-benzenedicarboxylic acid (5% water content, titre 95%, equal to 0.3 mol), 1440 g of water, 1.47 g of sulfuric acid. It is heated to 70° C. and 306.9 g (0.945 mol) of a 50% wt-ICl solution in 35% HCl are dropped during 1 h. The reaction is completed by keeping it under stirring at 70° C. for 4 h. It is cooled to 10° C., the precipitate is filtered and concentrated under reduced pressure. We obtained 144 g (86%) of a brownish crystalline solid formed by 5-amino-2,4,6-triiodo-1,3-benzenedicarboxylic acid containing 0.8% w/w of water and 1% of impurities coming from incomplete iodination.

EXAMPLE 5

Comparative example: 5-amino-2,4,6-triiodo-1,3-benzenedicarboxylic acid preparation according to the method described in Example 1 of JP-A-3197451, but without isolation of 5-amino-2,4,6-triiodo-1,3-benzenedicarboxylic acid.

The procedure of example 4 is repeated but instead of the isolated 5-amino-1,3-benzenedicarboxylic acid, an equivalent amount (580 g) of the solution containing 5-amino 1,3-benzenedicarboxylic acid sodium salt obtained at the end of hydrogenation is loaded. When the reaction is completed, a black suspension is given from which, through filtration, a modest amount (70 g) of a black solid formed by 5-amino-triiodo-1,3-benzenedicarboxylic acid heavily contaminated by impurities probably due to oxidation.

We claim:

1. A process for preparing 5-amino-2,4,6-triiodo-1,3-benzenedicarbooxylic acid, comprising the successive steps of:

(a) catalytically hydrogenating 5-nitro-1,3-benzenedicarboxoylic acid in a neutral or basic environment to yield an aqueous solution of 5-amino-1,3-benzenedicarboxylic acid sodium salt; and thereafter (b) directly iodinating the 5-amino-1,3-benzenedicarboxylic acid sodium salt solution of step (a), without purification, with a solution of ICl in the presence of both HCl and $H_2SO_4$.

2. The process according to claim 1, in which a ratio of the total equivalent acids provided by HCl and $H_2SO_4$ to the moles of 5-nitro-1,3-benzenedicarboxylic acid directly iodinated ranges from 2.5:1 to 3.5:1.

3. The process according to claim 2, in which the ratio of the equivalents of $H_2SO_4$ to the moles of 5-nitro-1,3-benzenedicarboxylic acid ranges from 0.5:1 to 3.5:1.

4. The process according to claim 3, in which the ratio of the equivalents of $H_2SO_4$ to the moles of 5-nitro-1,3-benzenedicarboxylic acid ranges from 2.0:1.

5. The process according to claim 1, in which the ratio of ICl to the moles of 5-nitro-1,3-benzenedicarboxylic acid directly iodinated ranges from 3.0:1 to 3.5:1.

6. The process according to claim 1, in which the molar ratio of HCl to ICl in the solution of ICl ranges from 0.4:1 to 1.2:1.

7. A process according to claim 1, in which the temperature of step (b) ranges from 75° to 110° C.

8. A process according to claim 7, in which the temperature of step (b) ranges from 70° to 95° C.

* * * * *